(12) United States Patent
Schaefer (10) Patent No.: US 8,758,291 B2
(45) Date of Patent: Jun. 24, 2014

(54) WOUND VENTILATION SYSTEM

(75) Inventor: Joseph H. Schaefer, Grafton, WI (US)

(73) Assignee: Acute Ideas, Inc., Grafton, WI (US)

(*) Notice: Subject to any disclaimer, the term of this patent is extended or adjusted under 35 U.S.C. 154(b) by 1050 days.

(21) Appl. No.: 12/537,755

(22) Filed: Aug. 7, 2009

(65) Prior Publication Data

US 2011/0034861 A1    Feb. 10, 2011

(51) Int. Cl.
*A61M 37/00*    (2006.01)
*A61M 35/00*    (2006.01)
*A61M 1/00*    (2006.01)

(52) U.S. Cl.
CPC ............. *A61M 1/0084* (2013.01); *A61M 35/00* (2013.01); *A61M 2205/18* (2013.01); *A61M 2205/3368* (2013.01); *A61M 2205/3653* (2013.01); *A61M 2205/3331* (2013.01); *A61M 2202/0208* (2013.01); *A61M 1/0088* (2013.01)
USPC .................. 604/23; 604/22; 604/543; 604/19

(58) Field of Classification Search
USPC .................................. 604/19, 22–23, 543, 24
See application file for complete search history.

(56) References Cited

U.S. PATENT DOCUMENTS

| | | | |
|---|---|---|---|
| 4,224,941 A | 9/1980 | Stivala | |
| 4,801,291 A | 1/1989 | Loori | |
| 4,911,357 A * | 3/1990 | Kitamura | 236/44 E |
| 5,029,579 A | 7/1991 | Trammell | |
| 5,154,697 A | 10/1992 | Loori | |
| 5,250,043 A | 10/1993 | Castellana et al. | |
| 5,512,041 A | 4/1996 | Bogart | |
| 5,636,643 A * | 6/1997 | Argenta et al. | 128/897 |
| 5,645,081 A | 7/1997 | Argenta et al. | |
| 5,735,833 A | 4/1998 | Olson | |
| 5,810,795 A | 9/1998 | Westwood | |
| 5,848,998 A | 12/1998 | Marasco, Jr. | |
| 5,865,722 A | 2/1999 | Heng | |
| 6,241,697 B1 | 6/2001 | Augustine | |
| 6,458,109 B1 | 10/2002 | Henley et al. | |
| 6,465,708 B1 | 10/2002 | Augustine | |

(Continued)

FOREIGN PATENT DOCUMENTS

| | | |
|---|---|---|
| WO | 9826826 | 6/1998 |
| WO | 0007653 | 2/2000 |

(Continued)

OTHER PUBLICATIONS

PCT International Search Report and Written Opinion for PCT/US2010/044582 (corresponding PCT application which claims priority to application being examined), mailed Nov. 15, 2010, 14 pages.

*Primary Examiner* — Edelmira Bosques
(74) *Attorney, Agent, or Firm* — Quarles & Brady LLP (57) ABSTRACT

A wound treatment apparatus that ventilates a wound dressing with warm humidified oxygen and/or air at a very low flow rate while under a sub-atmospheric pressure. A controlled flow of filtered air and/or oxygen is selected or blended under atmospheric pressure. This gas is pulled by a downstream vacuum source through a flow limiting device and exits at a sub-atmospheric pressure equal to the vacuum source. The gas flow is then humidified and heated to prescribed conditions before entering a substantially airtight negative pressure type wound dressing which is adapted for ventilation with an added inlet connection. This conditioned gas ventilates and nourishes the wound environment exiting the dressing outlet, through a fluid trap, to the vacuum source.

17 Claims, 3 Drawing Sheets

(56) References Cited

U.S. PATENT DOCUMENTS

| | | |
|---|---|---|
| 6,644,313 B2 * | 11/2003 | Prime et al. .............. 128/205.24 |
| 6,685,681 B2 | 2/2004 | Lockwood et al. |
| 6,752,794 B2 | 6/2004 | Lockwood et al. |
| 6,800,074 B2 | 10/2004 | Henley et al. |
| 6,855,135 B2 | 2/2005 | Lockwood et al. |
| 7,022,113 B2 | 4/2006 | Lockwood et al. |
| 7,066,902 B1 * | 6/2006 | Ott et al. ..................... 604/23 |
| 7,195,624 B2 | 3/2007 | Lockwood et al. |
| 7,198,046 B1 | 4/2007 | Argenta et al. |
| 7,216,651 B2 | 5/2007 | Argenta et al. |
| 7,276,051 B1 * | 10/2007 | Henley et al. ................ 604/304 |
| 7,534,927 B2 | 5/2009 | Lockwood et al. |
| 2005/0119607 A1 * | 6/2005 | Van Der Linden et al. ..... 604/23 |
| 2007/0209668 A1 | 9/2007 | Linton |
| 2007/0219532 A1 | 9/2007 | Karpowicz et al. |
| 2007/0282249 A1 | 12/2007 | Quisenberry et al. |
| 2008/0071330 A1 | 3/2008 | Quisenberry et al. |

FOREIGN PATENT DOCUMENTS

| | | |
|---|---|---|
| WO | 0232486 A1 | 4/2002 |
| WO | 2007062024 A1 | 5/2007 |
| WO | 2008/130689 A1 | 10/2008 |

* cited by examiner

WOUND VENTILATION SYSTEM

CROSS-REFERENCE TO RELATED APPLICATION

Not applicable.

STATEMENT REGARDING FEDERALLY SPONSORED RESEARCH OR DEVELOPMENT

Not applicable.

BACKGROUND OF THE INVENTION

Most wounds are small and heal quickly. This invention, however, is concerned with healing chronic wounds. A chronic wound is a wound that fails to heal in an orderly set of stages and in a reasonable amount of time. These wounds are difficult to treat, requiring much skill and many resources, and which may take months or even years to heal. Wounds that don't heal properly can lead to amputation and even loss of life. Common types of chronic wounds are leg ulcers, pressure ulcers (bedsores) and diabetic foot ulcers.

Leg ulcers occur due to impairment of the circulation in the leg. When veins are not functioning properly, the tissue surrounding those veins no longer receives an adequate supply of fresh blood. Oxygen cannot reach those tissues, leading to an open wound.

Pressure ulcers can occur in people of any age and are typically caused by staying in the same position for a prolonged period of time. Lying in bed or sitting in a wheelchair can put sustained pressure on the skin over a bony prominence. This pressure can cut off the blood supply and lead to a pressure ulcer or bedsore.

Diabetic foot ulcers are a common complication of diabetes. A diabetic can be unaware of a minor foot injury due to the loss of pain sensation associated with neuropathy. Continued walking on an unnoticed injury causes increased trauma and can lead to more serious injury that can become chronic.

Several million people are afflicted with chronic wounds every year. Elderly people have thinner skin which is more easily damaged; bed-ridden elderly people are at a particularly high risk. Chronic wounds that take months to heal or those that never heal, cause severe pain and hardship with much diminished quality of life. Complex wounds such as surgical wounds with complications, and burn wounds, also require additional procedures to achieve wound closure. All of these wounds represent major health burdens and drains on healthcare resources.

There are many known methods to treat chronic or complex wounds. Those relevant to this invention are: topical oxygen therapy; negative pressure wound therapy; moist wound therapy; and localized warming therapy.

Topical Oxygen Therapy

Topical oxygen therapy uses pure oxygen applied directly to the surface of the wound at a pressure slightly greater than atmospheric. The oxygen is usually supplied to an inflatable, see-through plastic bag with edges that adhere to the skin. The air-tight devices can be in the shape of a sleeve, boot or pouch. Oxygen is both a nutrient and an antibiotic, and an adequate supply is vital for each of the steps required for wound healing. Oxygen facilitates healing by suppressing the proliferation of bacteria, promoting tissue granulation, and accelerating epithelialization.

Stivala U.S. Pat. No. 4,224,941 and Loori U.S. Pat. No. 4,801,291 are good examples of topical oxygen therapy. Products using topical oxygen include O2Boot® and O2Sacral® by GWR Medical, Inc. and O2Misly™, by IYIA Technologies. Topical oxygen is not administered continuously as excess may cause other problems. Therapy is usually administered 90 minutes per day for four consecutive days, followed by a three day break. This protocol is then repeated as necessary until the wound is healed. Other oxygen-based therapies include hyperbaric oxygen chamber treatment, in which the oxygen is inspired; and the use of self-contained oxygen producing dressings.

Negative Pressure Wound Therapy

Negative pressure wound therapy applies localized negative pressure (vacuum) to the wound bed, promoting healing by sucking air and exudate from the wound. Excess fluids or exudate are known to be detrimental to the healing process. According to Kinetic Concepts, Inc., the other benefits of negative pressure wound therapy are: promoting the reduction in local edema; reducing infection risk; and stimulating the growth of healthy, vascularized granulation tissue.

Kinetic Concepts, Inc. markets the V.A.C.® (Vacuum Assisted Closure) System. This system uses a foam dressing cut to fit the size and shape of the wound, which is inserted into the wound. One end of a plastic tube is inserted into the foam dressing, while the other end is connected to a vacuum pump. An occlusive drape covers the wound and exiting tube, adhering to the skin surrounding the wound, making the dressing air-tight. When the pump is turned on, the negative pressure draws the edges of the wound together, and aspirates excess fluids from the foam dressing. The fluids are collected in a canister. Kinetic Concepts, Inc. is the assignee on numerous negative pressure wound therapy patents. One of the more recent is Argenta et al. U.S. Pat. No. 7,216,651.

Quisenberry et al. U.S. Pat. Application Publication No. US2008/0071330 A1 discloses a negative pressure wound therapy dressing which is combined with a pad comprising a plurality of light emitting diodes for treating the wound area. Karpowicz et al. U.S. Pat. Application No. US 2007/0219532A1 discloses a negative pressure pump system with a reference airflow.

Moist Wound Therapy

Moist wound therapy has been accepted as a major advance in the treatment of chronic wounds for more than 40 years. Any therapy that dehydrates the wound, such as dry gauze dressings, heat lamps, or exposure to air, is detrimental to chronic wound healing. When wounds dry out they form a scab which slows down the healing process. The principal function of a wound dressing is to provide a moist healing environment. Healing is stimulated and wounds heal faster if moisture is provided or maintained at the wound. Saline-soaked gauze that is kept moist is an effective wound dressing. There may be a delicate balance between keeping a wound moist and removing/absorbing excessive fluid from the wound. Excess fluid can delay healing and contribute to a maceration or breakdown of the skin.

Hundreds of dressings that help to create a moist wound environment are currently available. Examples of technologies that use moist wound healing are hydrogels, hydrocolloids, alginates, foams and films. Bogart U.S. Pat. No. 5,512,041 entitled "Wound Dressing for Promoting Moist Wound Healing" is one such example. This dressing is semi-occlusive, meaning it is vapor permeable and impermeable to liquids and bacteria. This dressing also has a pad which absorbs excess wound fluids (wound exudate). Henley et al. U.S. Pat. No. 7,276,051 entitled "Wound Treatment Apparatus" discloses a fluid supply and a fluid drainage in communication with a bandage cavity.

Localized Warming Therapy

Localized warming therapy, the use of mild heat for the treatment of chronic wounds, is known to have beneficial effects. A chronic wound is lacking in blood supply and typically becomes hypothermic. Even healthy extremities can be cool and their wounds more hypothermic. Hypothermia slows cellular function and biochemical reactions and is detrimental to healing. Mild heating dilates blood vessels, stimulating local circulation, increasing oxygen perfusion in tissues and accelerating wound healing.

People have used hot water bottles, heat lamps and heating pads for years, but accurate temperature control is lacking with these devices. Normal body temperature is 37 degrees C. Hyperthermia, higher than normal body temperatures, can be detrimental to the wound. Temperatures above 45 degrees C. can seriously damage healthy cells. Accurate control of temperature is very important to insure that no harm is done.

Augustine U.S. Pat. No. 6,241,697 discloses an electrically powered noncontact radiant heater enclosed within a wound dressing. An alternate embodiment uses heated air which passes through a dressing.

There are hundreds of companies, producing thousands of wound care products, using over a dozen different technologies. Besides those therapies cited above, other technologies include: antimicrobial silver dressings; collagen dressings; growth factors; skin substitutes; gene therapy; electrical stimulation; therapeutic ultrasound; electromagnetic therapy; low level laser therapy; nanotechnology products; honey-based dressings; and even maggot therapy. Many of these technologies and the products used are not approved for payment by insurance carriers, as their use is still considered to be experimental, investigational or unproven.

There are presently too many disparate technologies for the wound therapy marketplace. The currently available technologies with the best healing efficacy are still terribly ineffective in many cases. What is needed is higher healing efficacy and a method to significantly decrease the time needed to close these wounds. We need to help more people and improve their lives.

SUMMARY OF THE INVENTION

Years ago, wounds were thought to heal faster if they were left exposed to the air. Researchers then discovered that wounds so exposed were more susceptible to infection and would also dry out, forming a scab, which inhibited the healing process. Most all modern wound healing methods or technologies, including the four mentioned above, are designed to keep a wound in a closed environment preventing exposure to the air.

This invention teaches that a flow of fresh air can be therapeutic when done under controlled conditions. The environment within a wound dressing may become stale and depleted of oxygen. A flow of fresh air replenishes the oxygen and removes stagnant gasses, vapors, and odors which otherwise would accumulate under the wound dressing. A bacterial filter and active humidity control address potential problems.

The background of this inventor is in the heating, ventilating and air conditioning (H.V.A.C.) industry. This invention is a tiny specialized H.V.A.C. system to condition fresh air for use within a wound dressing. For years, H.V.A.C. systems have provided healthy environments for our bodies. Properly designed, an H.V.A.C. system can do the same for our wounds. This apparatus is designed to ventilate an airtight wound dressing with filtered warm humidified fresh air and oxygen while under a negative pressure. Unlike trying to combine the above four therapies, the ventilations system is the enabler to combine benefits attributed to these therapies. This new therapy is herein referred to as WOUND VENTILATION THERAPY.

Most ventilation systems use fans to create the air movement. This ventilation system uses the suction force from a therapeutic vacuum pump to provide the air movement.

The controlled variables of Wound Ventilation Therapy are: air flow, oxygen content, temperature, humidity, and negative pressure. This invention is designed to ventilate a wound dressing with these variables. It provides means to change these variables to suit an individual situation and the ability to administer all variables simultaneously.

It is the intent of Wound Ventilation Therapy that the healing benefits of each controlled variable will complement each other and become cumulative. It is also the intent of this invention that the efficacies of the individual controlled variables will also be cumulative. This comprehensive care would greatly improve the cure rates, speed up the time to cure, increasing the effectiveness of this new therapy and thereby decreasing the total costs involved.

A greenhouse is used to mimic the best of nature by providing plants with ideal conditions of temperature, humidity, sunshine and carbon dioxide content. Plants respond by being healthy and growing rapidly. It is the intent of this invention to mimic nature and accelerate the body's own natural healing process by engineering a protective wound environment. This environment would nourish the wound with precisely controlled natural conditions of fresh air, temperature, humidity, oxygen, and negative pressure.

The use of negative pressure wound therapy (N.P.W.T.) has become widespread in recent years because of its proven effectiveness. Enhancing N.P.W.T. with fresh air, oxygen, warmth and controlled humidity can only improve on this effectiveness.

Hyperbaric and topical oxygen wound therapies have been used successfully for years. This simple and novel apparatus is able to provide a hyperoxic wound environment without the need for elevated pressures. This oxygen treatment under negative pressure could be called "hypobaric oxygen" wound therapy. It is important that oxygen is not being inducted into a total vacuum, only a partial vacuum. A partial vacuum allows the oxygen to be therapeutic.

Almost all wound dressings are designed to provide a moist wound environment, but lack a control means; this can be problematic. This is the first known wound treatment apparatus to operate with active humidity control. All others are passive. The wound therapist sets a precise humidity level for the ventilation flow entering the wound. This setting is to be at a high enough level to prevent drying and low enough to prevent maceration of the skin. As an option, intentional condensate could be created to momentarily flush the wound.

A healthy human core body temperature is 37 degrees Centigrade. A wound on an extremity is often cooler which inhibits healing. Mild heating promotes healing by dilating the blood vessels at the wound site. This ventilation system allows the wound therapist to set a precise temperature, such as 37° C., for the ventilation flow entering the wound dressing.

Using different individual therapies on a wound usually requires costly dressing changes and exposes the wound to possible infection. This invention eliminates these problems as the therapies may be done simultaneously within the same dressing.

Therapies would not always have to be done simultaneously. When a patient with a portable wound vacuum unit desires to be ambulatory, the dressing inlet tube is removed and the open connection port is blocked, leaving only negative pressure therapy in use.

Another benefit of this invention is that the ventilation within the dressing is powered by an existing wound vacuum unit which may be selected based on price, suitability or preference. Likewise, this invention uses existing negative pressure wound dressings. There are several manufacturers and they offer many types and sizes for different applications. Again, the user has the choice based on suitability or preference.

The rule is "First, do no harm." The existing individual therapies referred to in this invention have been well-studied and their parameters are well known. It is therefore anticipated that safety precautions for these individual therapies will also be cumulative for this invention. The settings, limits, and safety considerations are to be based on clinical experience.

The primary components of this wound ventilation system are: a controllable flow of oxygen; a free flow of air; a ventilation flow rate controller; a heated humidifier; a re-heater; a negative pressure type of wound dressing; and a controlled source of vacuum.

Oxygen and filtered air are selected or blended under atmospheric pressure. This is accomplished by controlling the flow rate of the oxygen and allowing a free flow of air to make up the balance of the total flow. The total flow rate (liters/min.) is established by the ventilation flow rate controller. This provides the pressure differential necessary to create flow within the system. Flow enters this device at atmospheric pressure and exits at the negative pressure of the vacuum source. This ventilation flow rate is intended to be very low, so as to provide sufficient heat to warm most wounds to normal body temperature. The ventilation flow rate must also be well below the capacity of the vacuum source.

The purpose of the heated humidifier is to both heat the ventilation gasses and to fully saturate these gasses with sterile water vapor. The purpose of the re-heater is to minimize condensation in the insulated tubing that delivers these gasses to the negative pressure type wound dressing. To be therapeutic, these gasses are to enter the dressing inlet connection at a precisely controlled temperature and humidity. The temperature is to be at the normal body temperature of 37 C. (adjustable). The relative humidity should be adjustable within a range of about 80 to 100% R.H. The temperature set-point is maintained by controlling the operation of the re-heater. The relative humidity set-point is maintained by controlling the operation of the humidifier's heater.

The purpose of the controlled vacuum source is to both provide the negative pressure therapy and to provide the power source for the wound ventilation system.

The embodiment of this invention herein described, consists of the ventilation unit which is to be located bedside and which may be pole mounted. All of the ventilation unit components, with an internal flow of ventilation gasses are designed for single patient use. Other components such as a temperature control system for both the heated humidifier, and the re-heater, the operating controls, and monitoring controls are designed to be easily sanitized. This unit connects externally with an electrical power source, a tubing input from the oxygen source, an insulated tubing output to the wound dressing inlet, and an electronic input from a temperature sensor located at the wound dressing inlet connection.

This invention provides the means to set/control variables such as: oxygen content, ventilation flow rate, temperature, humidity, and negative pressure. The ability to independently control these variables along with their duration, allows a wound therapist to develop an individualized healing program for each patient.

DETAILED DESCRIPTION OF THE INVENTION

Figure 1:
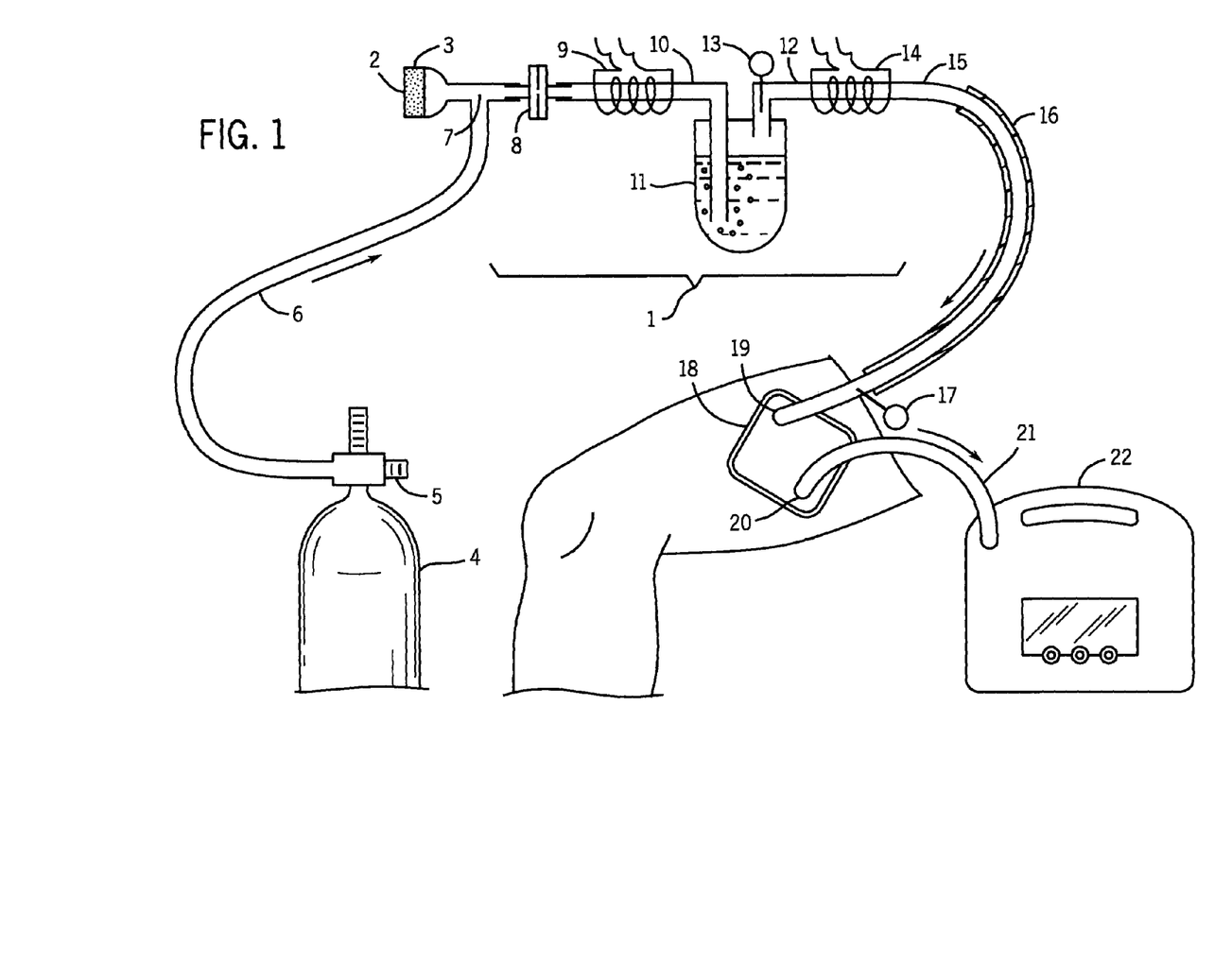
FIG. 1 is a schematic flow diagram of the ventilation system showing how it connects to the other wound healing components. Relative size of the ventilation system is much smaller than shown.

FIG. 1 is a schematic flow diagram of the vacuum powered ventilation system of this invention. This drawing shows the relationship between the ventilation system, the wound dressing, and the wound vacuum unit. This drawing also shows how these components are connected with each other as well as being connected with an oxygen source.

Referring to FIG. 1, there is shown a schematic of the ventilation system 1 in accordance with principles of this invention. This wound ventilation system is powered by the suction force created by a wound vacuum unit 22. Air used for ventilation is always available to be freely drawn in through the air intake 2 after passing through a bacterial filter 3. Oxygen, which is not administered continuously, is available for $O_2$ treatment sessions. Oxygen used for ventilation is sourced by either wall outlet oxygen or bottled oxygen 4. An adjustable pediatric (lower available flows) flow meter or other adjustable flow limiting means is used as the oxygen flow rate controller 5. The sum of the air and oxygen flow rates is the ventilation flow rate and is measured in liters/min. It is governed by a flow limiting device called the ventilation flow rate controller 8. During oxygen therapy sessions, the oxygen flow rate must be equal to or slightly greater than the ventilation flow rate to achieve a 100% oxygen flow. A 50% oxygen to air mixture would be achieved by setting the oxygen flow rate controller 5 to half that of the ventilation flow rate controller 8. Oxygen flow 6 through tubing, or other conduit, mixes with free air in the mixture plenum 7 under atmospheric pressure. An imbalance or a malfunction with oxygen flow is unable to build up pressure as it would flow freely out the air intake and maintain atmospheric pressure. The air/oxygen mixture flows freely as the suction force draws it into the ventilation flow rate controller 8. This device may be adjustable, but once a desired flow rate is known, a constant flow rate makes component design and control simpler. A good constant flow rate device is a filtered orifice flow restrictor. A filter protects the tiny orifice from plugging up. The ventilation flow rate is intended to be very low, at perhaps 0.2 to 0.5 liters/min. This flow rate needs to be high enough to sufficiently warm most wounds and low enough to be well below the capacity of the vacuum source. The ventilation flow rate controller 8 creates the pressure differential that sets a boundary between atmospheric pressure and the negative pressure created by the wound vacuum unit 22.

The purpose of the humidifier 11 and its heater 9 is to raise the wet bulb temperature of the ventilation gasses exiting the humidifier to a user-adjustable set point slightly below normal body temperature, such as 37° C. FIG. 1 shows the heater for humidifier 9 and the humidifier 11 as being separate components, with the humidifier shown as a simple diffusion bubble type. This was chosen for ease of explanation of this patent and is not meant to be a requirement. There are many types of heaters and humidifiers or heated humidifiers that could be used for the above-stated purpose. Some types use an IV type sterile water bag that drips the water by gravity into a humidifier cartridge. Heated humidifiers are typically used when supplying respiratory oxygen to a patient. They are available in many different designs that would be appropriate in this application, providing they were downsized for the much lower flow rates. The humidifier must be designed to produce water vapor only. Unlike mist or droplets, molecules of water vapor are too small to transport bacteria. The heated ventilation gasses 10 enter the humidifier 11 and pass through a diffuser which breaks the ventilation flow into tiny bubbles before passing through the sterile water disposed in the humidifier 11. These heated bubbles absorb water vapor before leaving the humidifier 11 at wet bulb temperature sensor 13. This sensor is to be fitted with a woven sock (not shown) which extends down into the water supply. This sock wicks up water which then evaporates in the gas at the sensor, thereby sensing actual wet bulb temperature. Preferably, if the humidifier design was such that complete saturation was all but assured, actual wet bulb sensing could be assumed with using only a dry bulb sensor at the same sensor location 13. This is because at 100% relative humidity or saturation, wet bulb and dry bulb temperatures are the same. Sensor 13 inputs a wet bulb temperature controller which controls the operation of the heater for humidifier 9. This wet bulb temperature controller maintains a user-adjustable set point slightly below normal body temperature, such as approximately 37° C.

Generally speaking, precise measurement of relative humidity is very difficult. The control scheme embodiment described here uses the relationship of wet bulb and dry bulb temperatures to indirectly control the relative humidity. A specific wet bulb and dry bulb temperature has a specific corresponding relative humidity. This can be plotted on a psychrometric chart and the relative data can be transferred to a simpler table for the wound therapist to use.

The heated and humidified ventilation gasses 12 enter the re-heater 14 and leave at location 15. The re-heater 14 is used to minimize any condensate that may form caused by the ambient cooling of the saturated ventilation gasses as they are transported to the wound dressing 18. Thermal insulation 16 on the dressing delivery tubing is used to reduce heat loss and to add control stability. An alternate embodiment to using this re-heater 14 and the thermal insulation 16 on the dressing delivery tubing would be to use a neonatal heated-wire breathing circuit typical to those used in respiratory care. This device uses a coiled heating element along the entire length of the dressing delivery tubing and would perform a similar re-heat function to minimize condensation. Either way, the dressing delivery tubing should be as short as possible.

Dry bulb temperature sensor 17 inputs the dry bulb temperature controller which controls the operation of the re-heater 14. This dry bulb temperature controller maintains a user-adjustable set point of 37 C at the sensor 17 which is located as close as possible or within the dressing inlet connection 19. Temperature sensors 13 and 17 are to be very precise, preferably to tenths of a degree, over a narrow range of normal body temperatures. The wound therapist is able to maintain the desired temperature of the gasses entering the dressing by adjusting the dry bulb temperature. The desired relative humidity of the gasses entering the dressing is maintained by adjusting the wet bulb temperature of the gasses leaving the humidifier. The dry bulb is usually set at normal body temperature of 37 C and the wet bulb is set slightly lower which lowers the relative humidity. If both were set the same, the relative humidity would be 100%.

Until the wound site warms up, there may be condensate forming within the dressing 18. This could be minimized with thermal insulation or a blanket placed over the dressing.

The wound dressing 18 used may be chosen from among the many available existing negative pressure dressings. Most likely it will be necessary to add an inlet tube connection 19 to the typical dressing. This connection should be added in a location non-adjacent to the existing outlet tube connection 20.

Dressing exit tubing 21 extends to the remotely located wound vacuum unit 22. This unit may be chosen from the many types available. The operation of this unit is to be as per the manufacturer's instructions. The added ventilation system is not meant to change any of the operational or safety requirements of the typical negative pressure wound therapy as recommended by the vacuum unit manufacturer.

Figure 2:
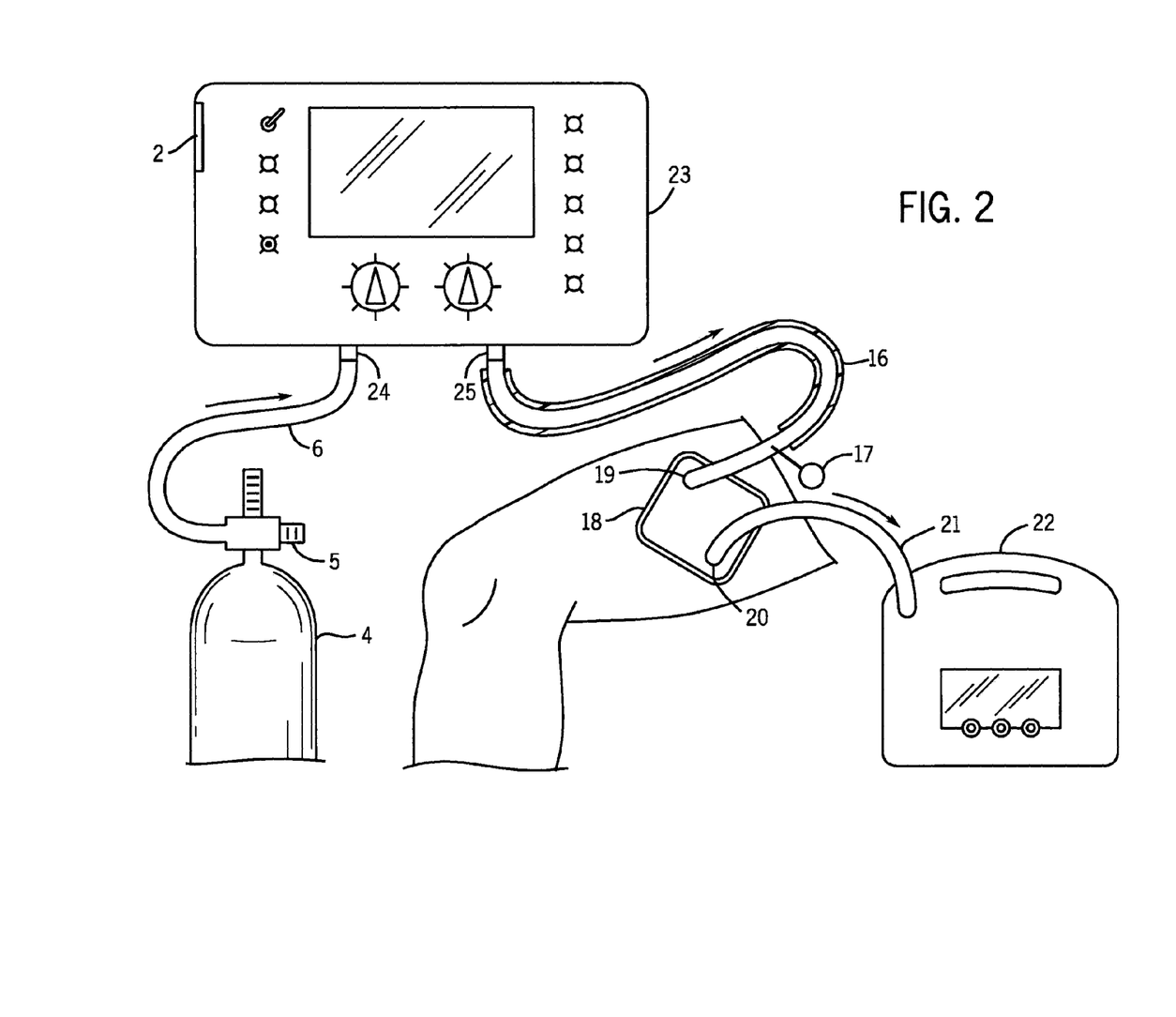
FIG. 2 is the ventilation system of FIG. 1 installed in an enclosure and comprising a ventilation system device. This drawing also shows the relationship of the ventilation device to the other wound healing components.
Figure 3:
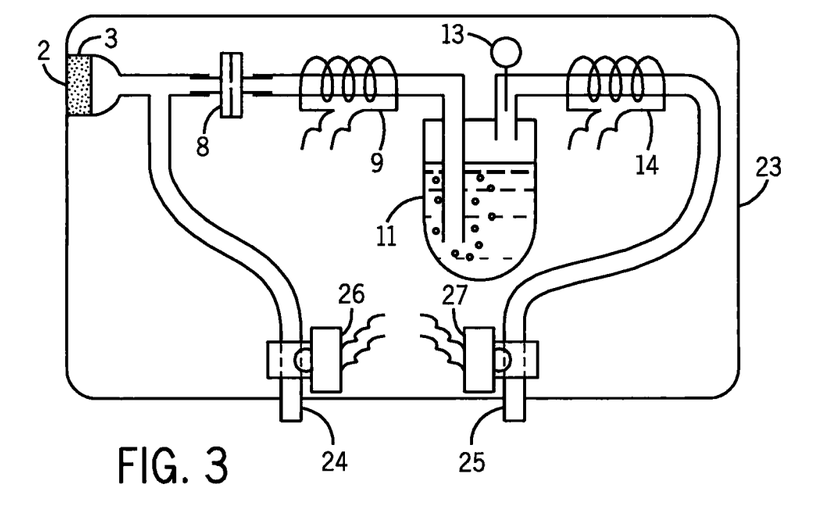
FIG. 3 is a schematic flow diagram of the preferred embodiment of the ventilation system device.
Figure 4:
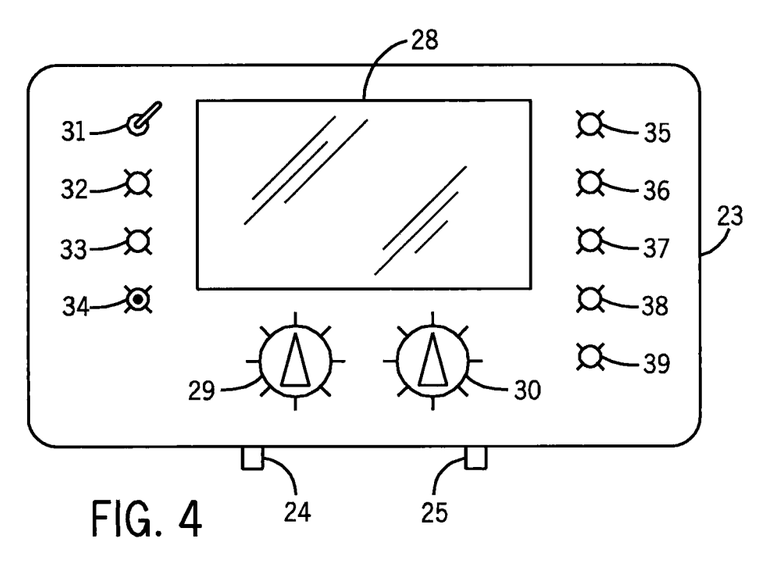
FIG. 4 is a front view of the preferred embodiment of the ventilation system device.

While FIG. 1 is used to show the basic components and the principles of operation of this invention, FIGS. 2, 3 and 4 are used to show how these components can be used together in a preferred embodiment of a ventilation system device. FIG. 2 shows the relationship of the ventilation device to the $O_2$ source, wound dressing, and the wound vacuum unit. FIG. 3 and FIG. 4 show the ventilation device in more detail. This preferred embodiment shown is one of many possible embodiments that could be constructed using these same principles of operation.

FIG. 2 shows the ventilation device 23 and the location of the ambient air intake 2. The $O_2$ inlet connection 24 and the ventilation device outlet connection 25 are also shown. Components 2 through 22 operate as described in FIG. 1. The ventilation device 23 may be mounted on an IV pole, mounted on a bed rail, or placed on a bed side table. It should be located close to the wound site. It requires an electrical power source from either an internal battery or a 120V power cord. The temperature sensor 17 either wired or wireless, needs to communicate with the ventilation device 23. If the ventilation device is able to communicate with the wound vacuum unit 22, a wireless or a wired connection must be provided.

FIG. 3 is the schematic flow diagram of the ventilation system of FIG. 1, installed inside of an enclosure and referred to as the ventilation device 23. Components 2 through 14 operate as described in FIG. 1. Again referring to FIG. 3, optional components not shown in FIG. 1 are an $O_2$ stop valve 26, a ventilation stop valve 27, and a programmable timer/display unit. These components are used to create the automated operation of the ventilation device in five different therapy modes:

A. 'Ventilate with $O_2$"
B. 'Ventilate with Air"
C. 'Ventilate with Flush"
D. "Negative Pressure Only"
E. "Negative Pressure Off"

The programmable timer/display unit and stop valves automate the sequence and duration of each therapy mode (A through E) to create an individualized patient program. Once programmed, the display unit would be able to graphically display the time and duration of the occurring therapy modes.

Referring again to FIG. 2, the $O_2$ stop valve 26 must be open for Mode A, 'Ventilate with $O_2$", to occur, and closed for all other therapy modes. Ventilation stop valve 27 must be open for one of the ventilate modes (A, B, or C) to occur and closed for Mode D, "Negative Pressure Only". To facilitate tubing replacement, for single patient use, both stop valves could be electrically actuated solenoid pinch valves. Mode C, 'Ventilate with Flush", is used to ventilate the wound with combined air and condensate at 37 C. During this mode, the re-heater 14 is shut off and the dry bulb sensor 17 is switched over to allow it to input the wet bulb controller and operate the heater for humidifier 9. The duration of this mode must be short as prolonged use could lead to maceration of the skin.

If the wound vacuum unit is operating on an intermittent cycle, Mode E, "Negative Pressure Off", will occur regardless of programming. To program Mode E, "Negative Pressure Off", it is necessary for the ventilation device to communicate with the wound vacuum unit.

Inside the ventilation device and not shown on the drawings, are the wet bulb temperature controller and the dry bulb temperature controller.

FIG. 4 is a front view of the ventilation device 23. The programmable timer/display 28 is a touch screen device that is used to program the sequence and duration of the desired therapy modes (A through E as previously described). The display screen also graphically displays time and duration of each occurring therapy mode. This display may also monitor and display such variables as dry bulb temperature entering the dressing, wet bulb temperature leaving the humidifier, temperature leaving the dressing, and relative humidity leaving the dressing. Dry bulb temperature adjustment 29 is used to enter the desired set-point for the temperature of the gasses entering the dressing. Wet bulb temperature adjustment 30 is used to enter the desired set-point for the wet bulb temperature of the gasses leaving the humidifier, which determines the relative humidity of the gasses entering the dressing. Both set-points are to be highly accurate to tenths of a degree over a very narrow range. Green L.E.D.'s 35-39 may be used to indicate the occurring therapy mode (A through E). The on/off switch 31 is used to turn on the electrical power for this ventilation device. A red L.E.D. 32 indicates an alarm condition for high temperature entering the dressing. Another red L.E.D. 33 is used to indicate an alarm condition for low relative humidity leaving the dressing. Push button 34 is used to silence the audible alarm. For safety, all heat sources should be disabled upon either an alarm condition or a loss of vacuum as sensed with a vacuum pressure switch.

The above described embodiment is only one of many possibilities. All described therapy modes may not be necessary. This ventilation device may be simplified with non-automated therapy modes using manual pinch valves and eliminating the programmable timer/display unit at least during early prototype testing.

Another embodiment of this invention could be designed to administer oxygen continuously. This would require that oxygen be at a low and safe concentration, perhaps 25, 30, or 35%. This would eliminate the need for separate therapy modes A and B. Since therapy modes C, D, and E are not necessary, another embodiment of this invention could be designed to operate in one constant mode. This would be a lot simpler and allow for a less costly ventilation device.

This described embodiment also shows a stand-alone ventilation device with the optional ability to communicate with the wound vacuum unit. Other embodiments could be created depending on the desired degree of integration of both ventilation and vacuum unit devices, up to and including designing all functions into a single device.

What is claimed is:

1. A wound ventilation system for treatment of a wound, the system comprising:
   a wound dressing having an inlet and an outlet, the wound dressing being configured to form a substantially airtight cover over the wound;
   including a free flow of air and a controlled flow of oxygen that passes through a mixture plenum to provide the gas at atmospheric pressure the gas being in communication with the inlet of the wound dressing;
   a vacuum source in communication with the outlet of the wound dressing, the vacuum source being configured to draw gas through the wound dressing;
   a gas flow controller disposed between the mixture plenum and the inlet of the wound dressing, the gas flow controller being configured to regulate the flow of gas drawn by the vacuum source and thereby establish less than atmospheric gas pressure between the gas flow controller and the vacuum source;
   a humidifier humidifying the gas entering the inlet of the wound dressing, the humidifier receiving and humidifying the gas at no more than atmospheric pressure;
   a heater located prior to an exit of said humidifier; and
   a re-heater located after said exit of said humidifier configured to heat the gas flowing to the wound and to minimize any condensate that may be formed.

2. The ventilation system of claim 1 in which the ventilation system is configured to provide five simultaneous therapies to the wound site, the five simultaneous therapies including fresh air, oxygen, negative pressure, warmth, and humidity.

3. The ventilation system of claim 2 in which the ventilation system is configured for separate adjustment of a rate of flow of the gas, an oxygen concentration in the gas, a negative pressure of the gas, a temperature of the gas, and a humidity level of the gas at the wound site to control the five simultaneous therapies.

4. The ventilation system of claim 1 in which a temperature controller includes a sensor that senses wet bulb temperature at an outlet of said humidifier, wherein said temperature controller controls the humidification of said gas by said humidifier.

5. The ventilation system of claim 4 in which the humidifier saturates the gas to 100% relative humidity at the sensor location, making the distinction between wet bulb and dry bulb temperature irrelevant, and enabling the temperature controller to sense an accurate dry bulb temperature, while assuming wet bulb, at the humidifier's outlet for controlling the humidifier.

6. The ventilation system of claim 4 in which a specified relative humidity is maintained by using its relationship to the settings of the wet bulb temperature and a dry bulb temperature.

7. The ventilation system of claim 1 in which a temperature controller senses dry bulb temperature at the wound dressing inlet for controlling the re-heater.

8. The ventilation system of claim 1 in which said humidifier provides a relative humidity above 100 % to flush the wound with warm condensate.

9. The ventilation system of claim 1 in which a high temperature safety controller senses temperature at the wound dressing inlet, and upon sensing a temperature above a predetermined level, provides an alarm and turns off all sources of heat.

10. The ventilation system of claim 1 including a vacuum pressure switch that provides a signal to turn off all sources of heat upon sensing a loss of vacuum in the ventilation system.

11. The ventilation system of claim 1 including a humidity sensor that senses relative humidity downstream of the humidifier, wherein upon sensing a humidity condition below a predetermined level activates an alarm.

12. The ventilation system of claim 1 in which said gas passes through a bacteria filter prior to entering said inlet.

13. The ventilation system of claim 1 in which the gas flow controller is selected from the group consisting of a filtered orifice flow restrictor, a needle valve, and a porous material having flow rate characteristics.

14. The ventilation system of claim 1 comprising an oxygen supply provided by at least one of a regulated and flow limited source from a compressed oxygen bottle and a regulated and flow limited source of wall outlet oxygen.

15. The ventilation system of claim 1 in which the humidifier uses sterile water.

16. The ventilation system of claim 1 including a programmable timer/display unit capable of recording total accumulated runtime of the ventilation system.

17. The ventilation system of claim 1 in which the vacuum source is part of a first unit and the gas flow controller, humidifier, and heater are part of a second unit which is separate from the first unit, but communicates with the first unit.

* * * * *

UNITED STATES PATENT AND TRADEMARK OFFICE
CERTIFICATE OF CORRECTION

PATENT NO.        : 8,758,291 B2                                    Page 1 of 1
APPLICATION NO.   : 12/537755
DATED             : June 24, 2014
INVENTOR(S)       : Joseph H. Schaefer It is certified that error appears in the above-identified patent and that said Letters Patent is hereby corrected as shown below:

In the Claims

Col. 10, Line 7, Claim 1, before "including" insert -- a gas --

Signed and Sealed this
Seventh Day of October, 2014

Michelle K. Lee
*Deputy Director of the United States Patent and Trademark Office*